(12) United States Patent
Pianca et al.

(10) Patent No.: US 8,660,664 B2
(45) Date of Patent: *Feb. 25, 2014

(54) METHODS FOR FORMING IMPLANTABLE MEDICAL DEVICES

(71) Applicant: Boston Scientific Neuromodulation Corporation, Valencia, CA (US)

(72) Inventors: Anne Margaret Pianca, Santa Monica, CA (US); Todd K. Whitehurst, Frederick, MD (US); James P. McGivern, Wakes Forest, NC (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/745,462

(22) Filed: Jan. 18, 2013

(65) Prior Publication Data

US 2013/0125395 A1    May 23, 2013

Related U.S. Application Data

(63) Continuation of application No. 10/503,281, filed as application No. PCT/US03/02784 on Jan. 29, 2003, now Pat. No. 8,364,278.

(51) Int. Cl.
*A61N 1/05* (2006.01)
*A61B 5/04* (2006.01)

(52) U.S. Cl.
USPC ...... 607/116; 607/2; 607/9; 600/36; 600/372; 600/373; 600/377

(58) Field of Classification Search
USPC ............. 600/36, 372, 373, 377; 607/2, 9, 116
See application file for complete search history.

(56) References Cited

U.S. PATENT DOCUMENTS

| 4,456,942 | A | 6/1984 | Bronikowski |
| 4,545,381 | A | 10/1985 | Bournay, Jr. et al. |
| 4,715,380 | A | 12/1987 | Harris |
| 5,000,177 | A | 3/1991 | Hoffmann et al. |
| 5,275,620 | A | 1/1994 | Darby et al. |

(Continued)

OTHER PUBLICATIONS

U.S. Appl. No. 10/503,281, Official Communication mailed Oct. 27, 2006.

(Continued)

*Primary Examiner* — Niketa Patel
*Assistant Examiner* — Christopher A Flory
(74) *Attorney, Agent, or Firm* — Frommer Lawrence & Haug LLP; Patrick R. Turner

(57) ABSTRACT

A method of forming an implantable medical device includes providing an implantable microstimulator. The microstimulator includes a body with a first end and an opposing second end. The microstimulator further includes internal circuitry that is disposed in the body and that provides stimulation energy. The microstimulator additionally includes a first microstimulator electrode that is electrically coupled to the internal circuitry and that is disposed along the first end portion of the body. The method further includes providing a first lead assembly that includes an insulated conductor with at least one first remote electrode disposed at a distal end of the insulated conductor, and a first connector disposed at a proximal end of the insulated conductor. The first connector is disposed over the first microstimulator electrode to completely cover the first microstimulator electrode. The first connector also electrically couples the insulated conductor to the first microstimulator electrode.

19 Claims, 6 Drawing Sheets

(56) References Cited

U.S. PATENT DOCUMENTS

| | | | |
|---|---|---|---|
| 5,730,628 A | 3/1998 | Hawkins | |
| 5,755,743 A | 5/1998 | Volz et al. | |
| 5,843,140 A | 12/1998 | Strojnik | |
| 6,164,284 A | 12/2000 | Schulman et al. | |
| 6,296,615 B1 | 10/2001 | Brockway et al. | |
| 6,321,126 B1 | 11/2001 | Kuzma | |
| 6,498,951 B1 | 12/2002 | Larson et al. | |
| 6,613,062 B1* | 9/2003 | Leckrone et al. | 606/167 |
| 6,634,364 B2* | 10/2003 | Westlund et al. | 128/898 |
| 7,096,070 B1 | 8/2006 | Jenkins et al. | |
| 7,949,395 B2* | 5/2011 | Kuzma | 607/36 |
| 8,204,595 B2 | 6/2012 | Pianca et al. | |
| 8,364,278 B2* | 1/2013 | Pianca et al. | 607/116 |
| 2002/0111663 A1 | 8/2002 | Dahl et al. | |
| 2003/0114905 A1 | 6/2003 | Kuzma | |
| 2004/0015205 A1* | 1/2004 | Whitehurst et al. | 607/48 |
| 2004/0225335 A1* | 11/2004 | Whitehurst et al. | 607/45 |
| 2005/0090883 A1 | 4/2005 | Westlund et al. | |
| 2005/0165465 A1* | 7/2005 | Pianca et al. | 607/116 |
| 2005/0165466 A1 | 7/2005 | Morris et al. | |
| 2005/0216070 A1* | 9/2005 | Boveja et al. | 607/46 |
| 2006/0184204 A1* | 8/2006 | He | 607/2 |
| 2007/0021800 A1* | 1/2007 | Whitehurst et al. | 607/45 |
| 2007/0100389 A1* | 5/2007 | Jaax et al. | 607/42 |
| 2008/0049376 A1* | 2/2008 | Stevenson et al. | 361/302 |
| 2008/0065183 A1* | 3/2008 | Whitehurst et al. | 607/116 |
| 2009/0005823 A1* | 1/2009 | Pianca et al. | 607/2 |
| 2010/0274325 A1* | 10/2010 | He | 607/61 |
| 2011/0152988 A1* | 6/2011 | Whitehurst et al. | 607/116 |
| 2011/0172679 A1* | 7/2011 | Kuzma | 606/129 |
| 2012/0316622 A1* | 12/2012 | Whitehurst et al. | 607/62 |
| 2013/0125395 A1* | 5/2013 | Pianca et al. | 29/874 |

OTHER PUBLICATIONS

U.S. Appl. No. 10/503,281, Official Communication mailed Jun. 7, 2007.

U.S. Appl. No. 10/503,281, Official Communication mailed Aug. 15, 2007.

U.S. Appl. No. 10/503,281, Official Communication mailed May 13, 2008.

U.S. Appl. No. 10/503,281, Official Communication mailed Nov. 13, 2008.

U.S. Appl. No. 10/503,281, Official Communication mailed Apr. 7, 2009.

U.S. Appl. No. 10/503,281, Official Communication mailed Aug. 11, 2009.

U.S. Appl. No. 10/503,281, Official Communication mailed Oct. 6, 2009.

U.S. Appl. No. 12/207,184, Official Communication mailed Sep. 21, 2011.

\* cited by examiner

METHODS FOR FORMING IMPLANTABLE MEDICAL DEVICES

CROSS-REFERENCE TO RELATED APPLICATIONS

This patent application is a continuation of U.S. patent application Ser. No. 10/503,281 filed on Mar. 11, 2005, which is a National Stage Entry of PCT/US03/02784 filed Jan. 29, 2003, all of which are incorporated herein by reference.

BACKGROUND OF THE INVENTION

The present invention relates to small implantable medical devices, and in particular to lead assemblies for such devices. Such small devices are easily implantable, and provide stimulation and/or sensing functions. The lead assembly is removably electrically connectable to an existing electrode of the device, thereby providing means to stimulate tissue, or sense physiological parameters, at some distance from the device.

Implantable electrical stimulation devices have proven therapeutic in a wide variety of diseases and disorders. Pacemakers and Implantable Cardiac Defibrillators (ICDs) have proven highly effective in the treatment of a number of cardiac conditions arrhythmias). Spinal Cord Stimulation (SCS) systems have long been accepted as a therapeutic modality for the treatment of chronic pain syndromes. Deep Brain Stimulation (DBS) has been applied in areas such as movement disorders. Functional Electrical Stimulation (FES) systems, such as the Freehand system by NeuroControl Corporation (Cleveland, Ohio), have been applied to restore some functionality to paralyzed extremities in spinal cord injury patients.

Current implantable electrical stimulation systems typically consist of a leaded system wherein the electrodes are on a lead and are separate from but connected to a System Control Unit (SCU) that contains the power source and the stimulation electronics. A number of these systems have the advantage of having fixation devices for the electrodes, so that the electrodes remain proximal to or even attached to their target sites of stimulation. For example, some pacemaker electrode leads have tines that act as barbs to hook Into the tissue, thereby anchoring the electrodes in place. As another example, the electrode used in the Neuro Cybernetic Prosthesis (NCP®) manufactured by Cyberonics (Houston, Tex.) is a helical electrode that is wound around the vagus nerve in order to remain attached to its stimulation target. In addition, several companies and research institutions, such as Neuro Stream Technologies, Inc. (Anmore, British Columbia, Canada) are investigating cuff electrodes, which wrap around the nerve like a cuff, thereby fixing an electrode(s) in close approximation to a nerve.

A microminiature electrical stimulator known as the BION® microstimulator has been developed to overcome some of the disadvantages of a large SCU-based (a.k.a. IPG-based) system. The BION® microstimulator is a leadless device, wherein the SCU and the electrodes have been combined into a single microminiature package. The current embodiment of the BION® microstimulator is a cylinder that is approximately 3 mm in diameter and between about 2 and 3 cm in length. This form factor allows the BION® microstimulator to be implanted with relative ease and rapidity, e.g., via endoscopic or laparoscopic techniques. Thus, the BION® microstimulator may easily be implanted subcutaneously, and in such a configuration, it is unlikely to demonstrate problems with cosmesis or erosion.

A known microminiature electrical stimulator, a microstimulator, is described in U.S. Pat. No. 5,193,539 issued May 16, 1993 for "Implantable Microstimulator." A method for manufacturing the microstimulator is described in U.S. Pat. No. 5,193,540 issued May 16, 1993 for "Structure and Method of Manufacturing of an Implantable Microstimulator." Further teaching is included in U.S. Pat. No. 5,324,316 issued Jun. 28, 1994 for "Implantable Microstimulator." The '539, '540, and '316 patents are incorporated herein by reference.

In some applications, e.g., pudendal nerve stimulation for the treatment of incontinence, the leadless BION® microstimulator system has proven sufficient. In such applications, the BION® microstimulator is surgically placed near an easily identifiable landmark(s), e.g., the pudendal canal. Additionally, in such applications the stimulator is surrounded by soft tissue and is not embedded in or located very close to large muscles or other structures that may demonstrate significant motion or varying pressure.

However, for other applications, a leadless BION® microstimulator may prove insufficient or inappropriate. For example, it may be desirable to implant a BION® microstimulator close to the skin, to facilitate power and/or data transfer, and/or to facilitate removal and/or replacement, while a lead assembly removably attached to the BION® microstimulator may stay in place, with the electrode(s) positioned for appropriate tissue stimulation, possibly deep within the body.

What is needed are lead assemblies for microdevices which facilitate removal and/or replacement of the microdevice by reducing or eliminating the ingress of fluids into the assemblies.

SUMMARY OF THE INVENTION

The present invention addresses the above and other needs by providing a lead assembly for small implantable medical devices (e.g., microdevices). Such microdevices may provide either or both tissue stimulation and sensing functions. Known microdevices include spaced apart electrodes on the outer surface of the microdevice. In some cases, the microdevice may not be locatable in contact with tissue targeted for stimulation or sensing, and the electrodes on the outer surface of the microdevice are not able to provide the intended stimulation or sensing. A connector of the lead assembly is over an electrode on the microdevice case, and electrically connects to an electrode(s) on a lead, thus providing a capability to stimulate or sense tissue not in contact with the microdevice. The lead assembly connector may partially or completely cover the electrode, wherein by completely covering the electrode, the electrode is Insulated from adjacent tissue.

The lead assembly includes an electrode(s), an insulated lead, and connector, The electrode is constructed from a biocompatible material, and may be in a variety of shapes. The electrode lead includes one or more wires to carry signals between the electrode(s) and the microdevice. The connector is removably connectable to the microdevice, and preferably provides a low resistance electrical connection between the wires and an electrode on the microdevice case.

In accordance with the invention, there is provided an electrode lead assembly that may be removably attached to a microstimulator or microsensor, for purposes of allowing stimulation or sensing at sites distal from the microdevice, in applications where the microdevice may not reside proximal to such sites. It is an object of the present invention to provide an assembly that inhibits fluid ingress white the assembly is not attached to a microstimulator or microsensor.

BRIEF DESCRIPTION OF THE DRAWINGS

The above and other aspects, features and advantages of the present invention will be more apparent from the following more particular description thereof, presented in conjunction with the following drawings wherein:

FIG. 6b shows an and view of the lead assembly of FIG. 6a;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
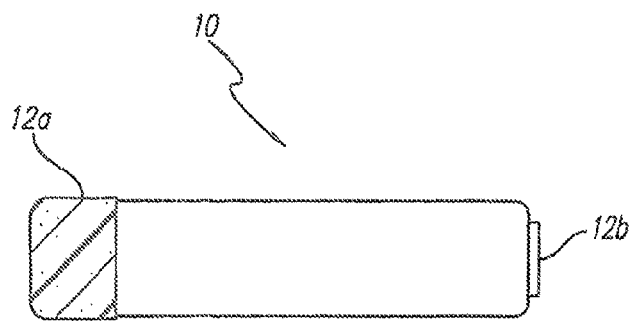
FIG. 1 shows a side view of a typical microdevice (a microstimulator of a microsensor), including electrodes at each end of the device.

Implantable microdevices may serve many useful purposes through stimulating nerves, muscles, or other tissue (a microstimulator), or through sensing various physiological conditions (a microsensor) within a patient. Such a microdevice 10 is shown in FIG. 1. The microdevice 10 includes Internal circuitry to receive and process signals, and to provide either sensing or stimulation through a first microdevice electrode 120 at one end, and a second microdevice electrode 12b at an opposite end. The microdevice 10 is very small to allow minimally invasive implantation. A representative microdevice 10 is about 2 to 3 cm in length, and about 3 mm in diameter. The characteristics, employment, and manufacturing of one example of a microdevice 10 are described in U.S. Pat. No. 6,193,539 issued May 16, 1993 for "Implantable Microstimulator," U.S. Pat. No. 5,193,540 issued May 16, 1993 for "Structure and Method of Manufacturing of an Implantable Microstimulator," and U.S. Pat. No. 5,324,316 issued Jun. 26, 1994 for "Implantable Microstimulator."

Figure 2:
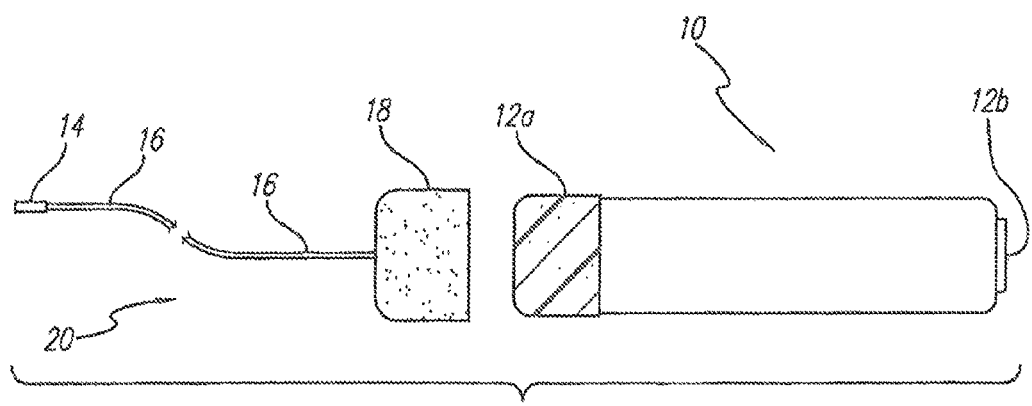
FIG. 2 depicts a microdevice and a lead assembly according to the present invention.

A lead assembly 20 according to the present invention is shown in FIG. 2 detached from the microdevice 10. The lead assembly comprises at least one remote electrode 14, a lead 16 including at least one wire (or conductor), and a connector 18. The remote electrode 14 provides stimulation or sensing at sites where the microdevice 10 would not normally reside due to a variety of reasons. The remote electrode 14 is fabricated from a biocompatible material(s) with a relatively low impedance, e.g., platinum, iridium, titanium, and alloys and preparations thereof. The remote electrode 14 may be fabricated to have a number of different shapes, e.g., a ball electrode, a cylindrical electrode, a disc electrode, a flat rectangular electrode, or an electrode curved around a surface of a nerve cuff. The remote electrode 14 preferably has sufficient surface area so as to ensure that safe level electric current density and electric charge density are maintained during chronic stimulation.

The remote electrode 14 may additionally or alternatively provide a means for sensing nerve signals (e.g., EEG, ENG), muscle signals (e.g., EMG), cardiac signals (e.g., ECG), or other state of the patient. In such embodiment, at least one electrode may be dedicated for recording and may have a surface area that is smaller than that used for stimulation, in order to provide a higher degree of spatial localization for recording. Additionally, the remote electrode 14 may be coated with materials such as platinum black, titanium nitride, carbon, or iridium oxide to increase the effective sensing area of the remote electrode 14 without increasing the geometric surface area.

The lead 16 connecting the remote electrode 14 to the connector 18 is fabricated from a biocompatible material(s), and the lead 14 insulates at least one wire that runs from the connector 18 to the remote electrode 14. Preferable materials include polymers such as silicone, and polyurethane, or preparations thereof. In the case where there is more than one remote electrode 14, the wires electrically connected to each electrode must be insulated from each other. The individual wires may be insulated from each other using a coating such as TEFZEL® (ethylene tetrafluoroethylene), TEFLON® (polytetrafluoroethylene), KYNAR® (polyvinylidene fluoride), PFA (perfluoralkoxy), FEP (fluorinated ethylene propylene), or HYTREL® (thermoplastic elastomer). Coating the outer surface of the lead and/or the outer surface of a guidewire during implantation may facilitate placement of the lead. For example, the outer insulation of the lead may be coated with a hydrophilic agent such as polyvinylperolydone (PVP).

Connector 18 is located at the proximal end of electrode lead 16 and electrically connects the wire(s) in the electrode lead 16 to at least one of the electrodes 12a, 12b of the microdevice 10, while mechanically attaching to the microdevice 10. In a preferred embodiment, connector 18 attaches a single stimulating remote electrode 14 at the distal end of the lead 16 to a single microdevice electrode 12a or 12b located on the microdevice 10. Preferably, the connector 18 completely covers the electrode 12a or 12b and ideally provides a watertight seal, thereby ensuring that most or all stimulation current is directed to the remote electrode 14. Connector 18 preferably provides good contact between the electrode 12a or 12b and the wire in the lead 18, ensuring a low electrical resistance connection between the electrode 12a or 12b and the wire.

Figure 3:
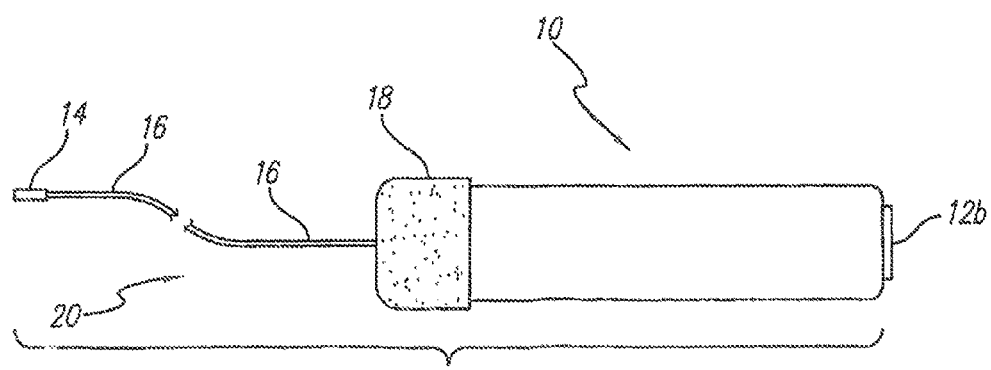
FIG. 3 shows the lead assembly connected to the microdevice.

Lead assembly 20 is shown connected to microdevice 10 in FIG. 3. As shown, the end of microdevice 10 is inserted into connector 18, which connector entirely covers and provides a seal around electrode 12a in order to prevent current from leaking from electrode 12a into nearby tissue. Lead assembly 20 may alternatively be connected to the second electrode 12b. Further, two lead assemblies 20 may be attached to a single microdevice 10 to provide two remote electrodes. The lead and/or remote electrode 14 may further Include a means of fixation to anchor the lead and/or electrode adjacent to a target site.

The lead assembly electrical/mechanical connection method allows for relatively easy attachment of lead assembly 20 to microdevice 10. The electrical/mechanical connection method may comprise one or more of a multiplicity of connecting methods including: a threaded connection, such as a set-screw mechanism; a clip connection; a ball bearing connection; a spring loaded connection; a conductive adhesive connection; a collet connection; a ball seal connection; and an interference fit connection.

In accordance with the invention, connector 18 preferably collapses or closes when a microdevice 10 is not inserted into connector 18, ensuring minimal fluid ingress into the portion of the connector 18 that makes electrical contact with the electrode 12a or 12b, i.e., electrical contact 22. In an alternative embodiment, a plug may be Inserted into the connector 18 when a microdevice 10 is not attached.

Figure 4A:
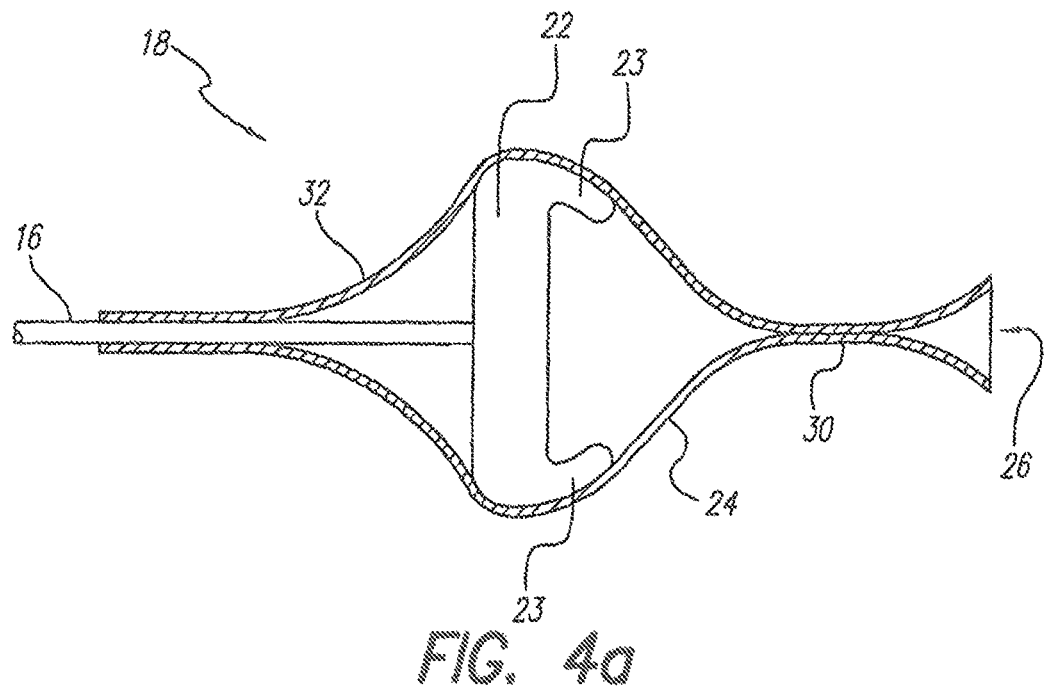
FIG. 4a illustrates a cross sectional view of an embodiment of a lead assembly of the invention.
Figure 4B:
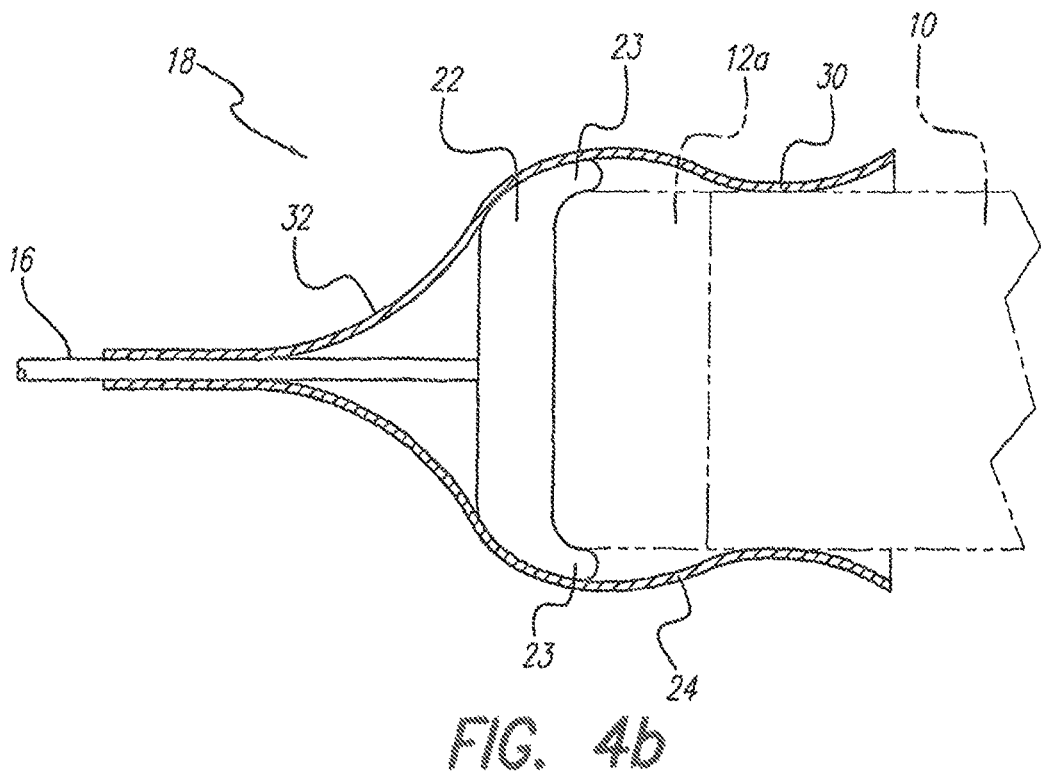
FIG. 4b shows the lead assembly of FIG. 4a with a microdevice inserted into the lead assembly.

FIGS. 4a and 4b show one embodiment of the invention. Connector 18 comprises an elastic pouch 24 that expands from a collapsed position, shown in FIG. 4a, as microdevice 10 is inserted at opening 26. FIG. 4b shows connector 18 with microdevice 10 inserted, so that electrode 12a makes electrical contact with contact 22. In this embodiment, connector 18 inhibits fluid ingress while in a collapsed state due to the properties of the material of pouch 24. For instance, pouch 24 may be made of a biocompatible elastic material(s) such as silicone or polyurethane which collapses when not expanded by microdevice 10, and seals as a result of the high coefficient of friction of the material, which causes the material to adhere to itself to form closure 30.

Additionally or alternatively, suture material or the like (not shown) may be provided at closure 30. For instance, sutures built into pouch 24 may encircle closure 30 so the ends of the sutures may be pulled and secured, in a drawstring manner. Thus, a surgeon may further tighten the seal at closure 30, when collapsed or when a microdevice 10 is inserted into connector 18. Suture material may additionally or alternatively be applied around pouch 24 at closure 30, rather than being provided therein.

As depicted in FIGS. 4a and 4b, the material of pouch 24 may extend around contact 22 and over a portion of lead 16. This portion 32 insulates surrounding tissue from contact 22 and provides stress relief and strength to the connection made between lead 16 (i.e., the wire in lead 18) and contact 22. This connection may be made via laser welding or other methods known to those of skill in the art. Insulation portion 32 may alternatively conform to the shape of contact 22, or may be otherwise configured to insulate surrounding tissue from contact 22.

As is also shown in FIGS. 4a and 4b, contact 22 may be configured with edges 23 that extend at least partly around electrode 12a when microdevice 10 is inserted, and which may also aid in sealing pouch 24 when collapsed. For instance, contact 22 and/or edges 23 may be made, at least in part, of a conductive material with resilient properties, such as 316 SS, 304 SS, or inconel. Edges 23 may, in a relaxed state, bend inward, aiding pouch 24 to seal at closure 30. Upon insertion of microdevice 10, edges 23 bend outward with pouch 24, allowing microdevice 10 to make electrical contact with contact 22.

Figure 5A:
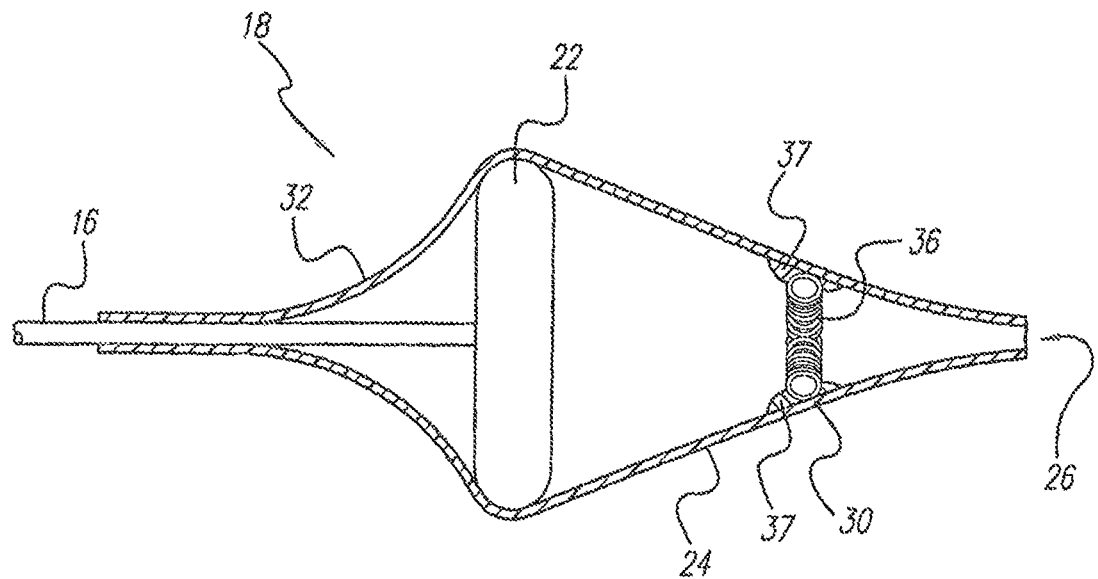
FIG. 5a illustrates a cress sectional view of an embodiment of a lead assembly of the invention which assembly includes a circumferential spring.
Figure 5B:
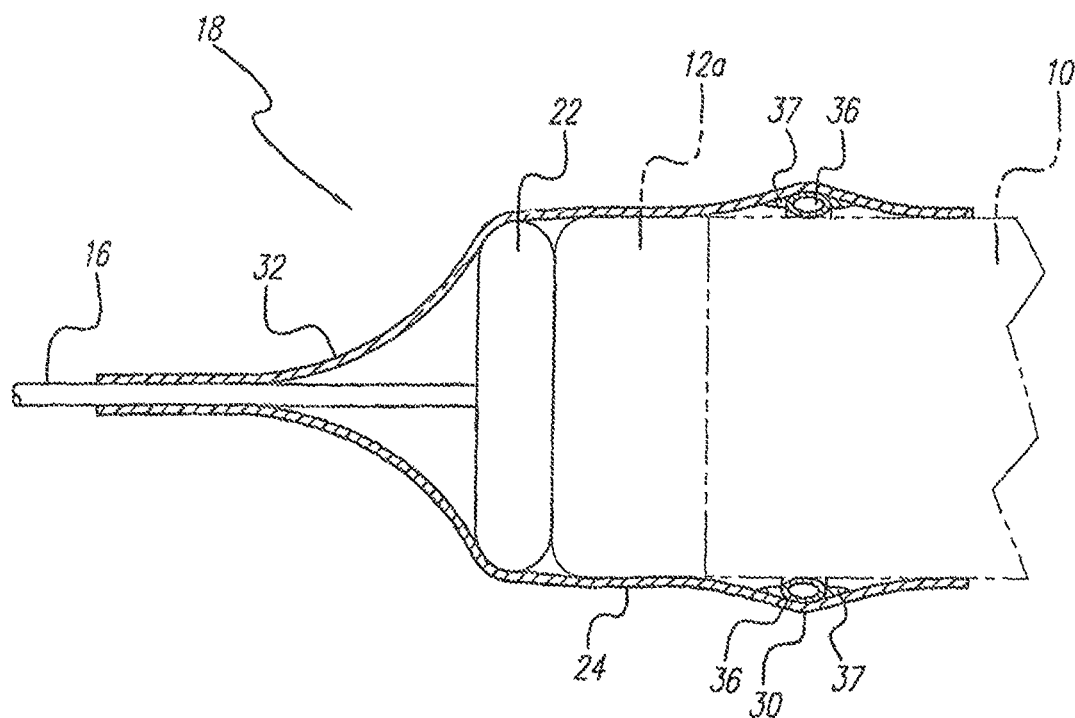
FIG. 5b shows the lead assembly of FIG. 4a with a microdevice inserted into the lead assembly.

In the embodiment illustrated in FIGS. 5a and 5b, closure 30 may include a circumferential spring 36 (such as manufactured be Bal Seal Engineering Company of Santa Ana, Calif.). To aid in sealing connector 18 when collapsed, spring 36 ray be coated with, for instance, silicone. In FIG. 5a, closure 30 is partially closed, and spring 36 is partially sealed. When connector 18 is collapsed and fully closed, the coils of spring 36 compress against each other to form a seal. Spring 36 may be positioned via attachment to pouch 24 via a medical adhesive or the like at one or more attachment points 37, and preferably three or more points 37.

As with the other closure embodiments herein, the closure, in this case spring 36, aids in capturing and retaining microdevice 10 in place when inserted in connector 18. Furthermore, closure 30 may aid in sealing connector 18 around electrode 12a in order to prevent current from leaking from electrode 12a into nearby tissue.

In this or other embodiments of the invention, contact 22 may be made of a spring, such as a circumferential spring, or other useful configuration. In addition or alternatively to contact 22, electrical contact with electrode 12a (or other electrode) may include a portion or portions of connector 18, such as a portion or portions of pouch 24 that make electrical contact with the electrode and are electrically connected to the wire(s) in lead 16. Any such electrical connection may further aid in retaining microdevice 10 and/or in sealing connector 18 around electrode 12a.

Figure 6A:
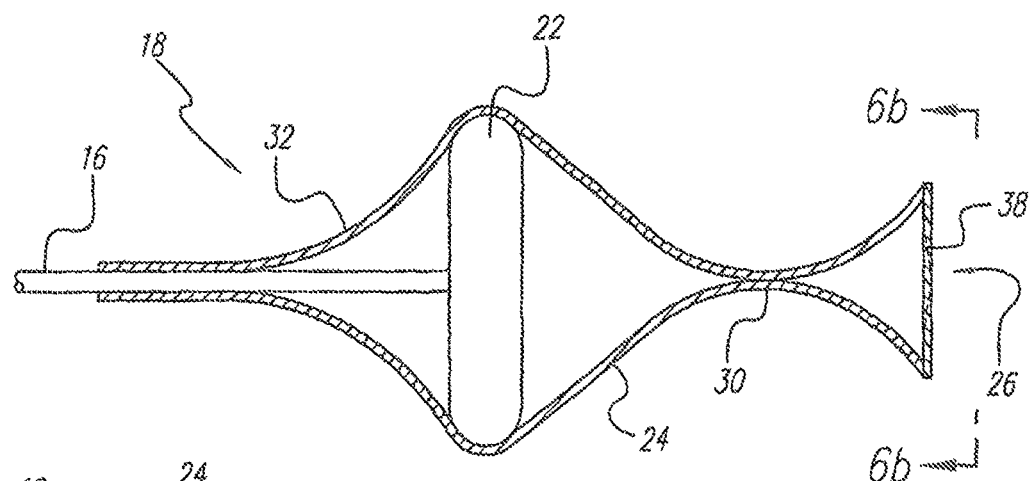
FIG. 6a illustrates a cross sectional view of an embodiment of a lead assembly of the invention which assembly Includes a seal.
Figure 6B:
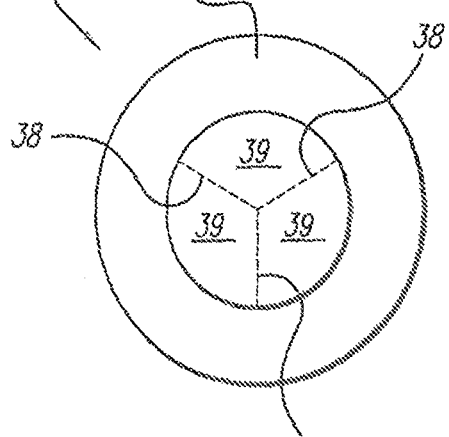
Figure 6C:
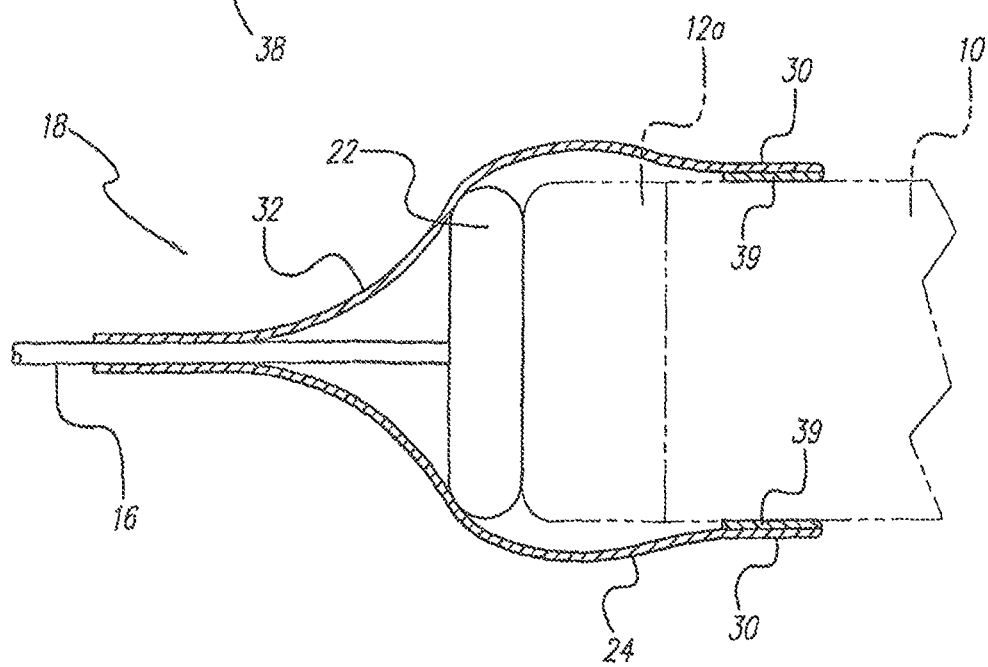
FIG. 6c shows the lead assembly of FIG. 4a with a microdevice inserted Into the lead assembly.

In the embodiment shown in FIGS. 6a, 6b, and 6c, closure 30 may include a seal 38, which seal may be positioned at opening 26 or other position on connector 18. As can be seen in FIG. 8b, seal 38 may preferably include three or more flaps 39, which allow insertion and removal of microdevice 10, and which, when microdevice 10 is not present, fit closely together to inhibit ingress of fluids into connector 18. Any suitable seal design made of biocompatible materials, such as silicone or polyurethane, as known to those of skill In the art, may be used. As with other embodiments herein, seal 38 may be provided in addition or as an alternative to the pouch 24 being made of a biocompatible elastic material(s) such as silicone or polyurethane, which collapses when microdevice 10 is not present, and seals as a result of the inherent adhesive properties of the high coefficient of friction material, which adheres to itself to form closure 30.

Figure 7A:
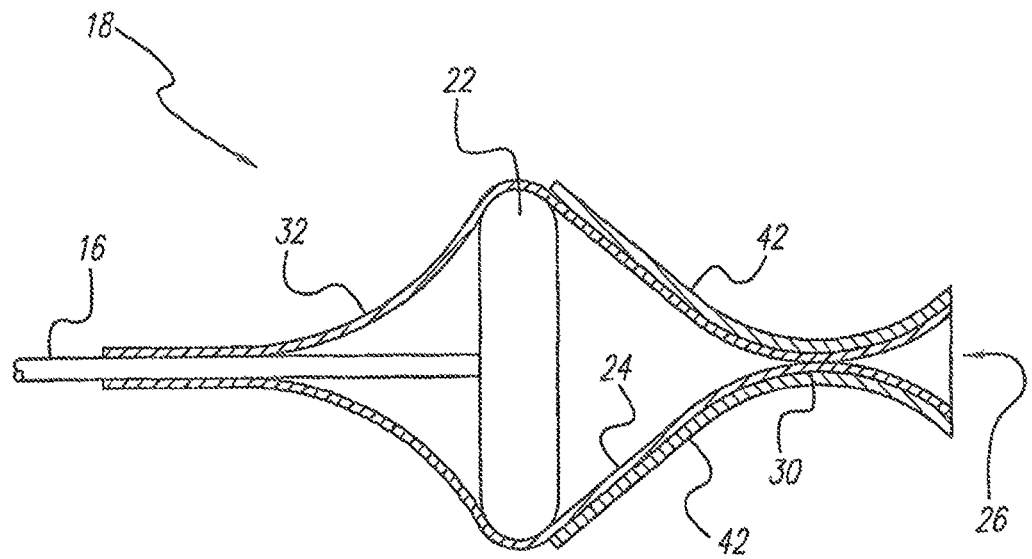
FIG. 7a illustrates a cross sectional view of an embodiment of a lead assembly of the invention which assembly Includes leaf springs.
Figure 7B:
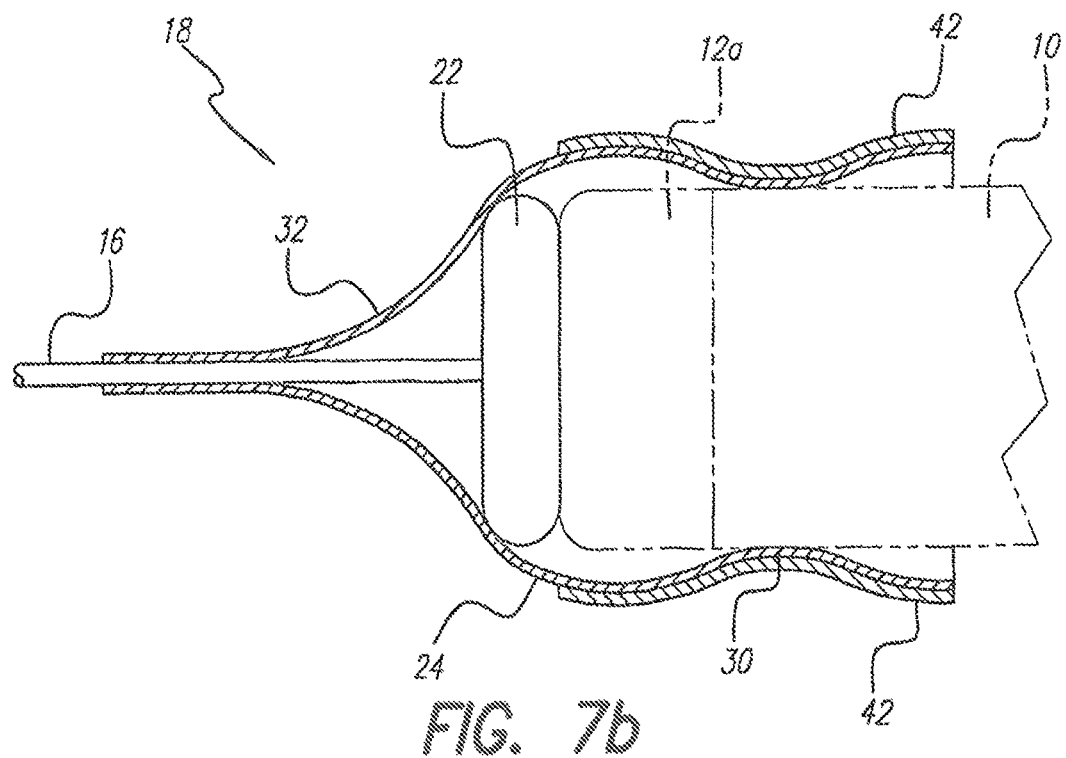
FIG. 7b shows the lead assembly of FIG. 4a with a microdevice inserted into the lead assembly.

As shown in the embodiment of FIGS. 7a and 7b, closure 30 may include leaf spring(s) 42, preferably Incorporated longitudinally in the walls of pouch 24. As with other embodiments herein, leaf springs 42 aid in sealing closure 30 and inhibiting ingress of fluids when connector 18 is collapsed and may also aid in retaining microdevice 10 when inserted and/or in sealing connector 18 around electrode 12a.

Connector 18 may be made by conventional methods known in the art. For instance, connector 18 of FIGS. 7a and 7b may be made by placing contact 22, springs 42, and possibly also the proximal end of lead 16 in a mold and injection molding (i.e., insert molding) the pouch 24 material (and/or portion 32), such as silicone, polyurethane, TEFLON® (polytetrafluoroethylene), or the like, around the inserts, thus forming the connector 18 with leaf springs 42 and contact 22 integral thereto. Other methods known in the art may be used for this or other embodiments herein, such as blow molding and/or securing closure devices, such as leaf springs 42 or circumferential spring 36, to connector 18 with a medical adhesive or the like, as described and shown earlier.

Figure 8:
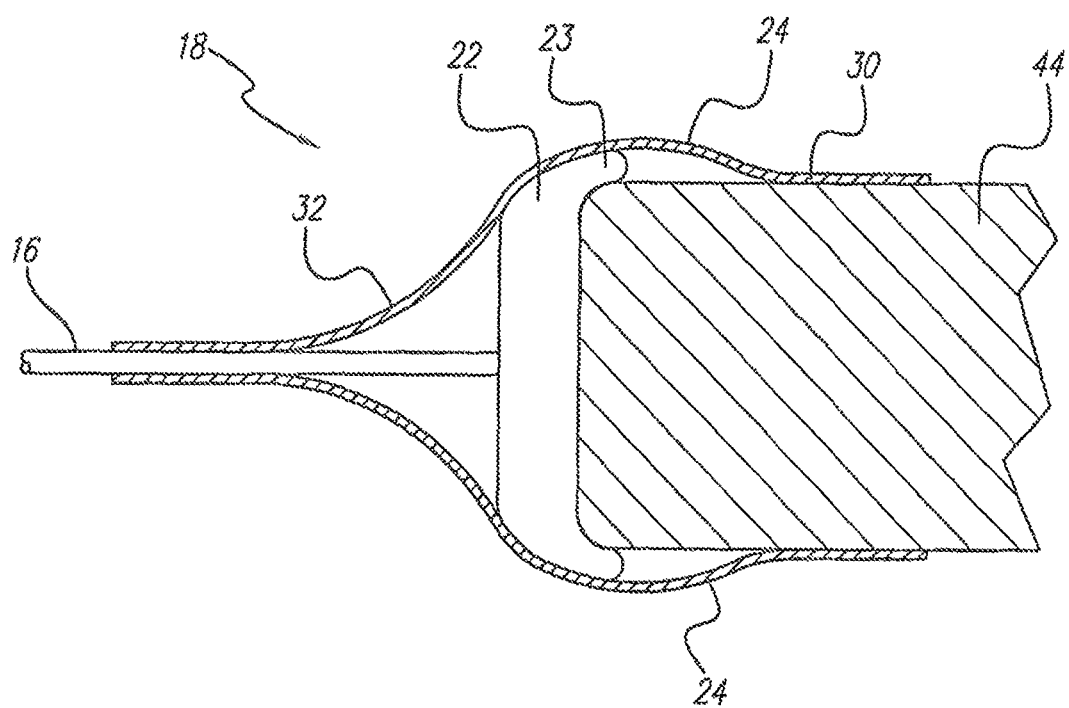
FIG. 8 illustrates a cross sectional view of an embodiment of a lead assembly of the invention which assembly includes a plug.

In an alternative embodiment, as shown in FIG. 8, a plug 44 may be used to protect contact 22 from fluids when microdevice 10 is not present in connector 18. Such plug 44 configuration and size may be similar to microdevice 10, or may include features to aid in insertion, removal, and/or sealing of connector 18. For instance, plug 44 may be slightly larger than microdevice 10, which may improve the seal created when plug 44 is inserted into connector 18. As another example, plug 44 may include features such as surface texturing to aid in sealing and/or handling of plug 44. Plug 44 may be made of any suitable biocompatible material(s), such as silicone, polyurethane, or TEFLON® (polytetrafluoroethylene).

Those skilled in the art will recognize variations of the embodiments described herein. For instance, various closure embodiments may be combined to further inhibit ingress of fluids into connector 18. The heart of the present invention is a lead assembly that may be removably attached to a microdevice, which lead assembly inhibits fluid ingress when the microdevice is removed from the connector of the lead assembly. Any lead assembly which provides this capability to a small implantable microdevice is intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed and desired to be protected by U.S. Letters Patent:

1. A method of forming an implantable medical device, the method comprising:
   providing an implantable microstimulator, the microstimulator comprising a body having an elongated shape with a first end portion and an opposing second end portion, the microstimulator further comprising internal circuitry that is disposed in the body and that is configured and arranged for providing stimulation energy, and a first microstimulator electrode that is electrically coupled to the internal circuitry and that is disposed along the first end portion of the body;
   providing a first lead assembly, the first lead assembly comprising an insulated conductor having a proximal end and an opposing distal end, at least one first remote electrode disposed at the distal end of the first lead assembly and a first connector disposed at the proximal end of the insulated conductor, the first connector comprising a pouch of elastic biocompatible material configured and arranged to completely cover the first microstimulator electrode when the first connector of the first lead assembly is disposed over the first microstimulator electrode and to seal the first connector when the first connector of the first lead assembly is not disposed over the first microstimulator electrode; and
   disposing the first connector of the first lead assembly over the first microstimulator electrode to completely cover the first microstimulator electrode and to electrically couple the insulated conductor of the first lead assembly to the first microstimulator electrode.

2. The method of claim 1, wherein providing a first connector that comprises a pouch of elastic biocompatible material configured and arranged to seal the first connector comprises providing suture material configured and arranged to aid in sealing the first connector when the first connector of the first lead assembly is not disposed over the first microstimulator electrode by wrapping around at least a portion of the pouch.

3. The method of claim 1, wherein providing a first connector that comprises a pouch of elastic biocompatible material configured and arranged to seal the first connector comprises providing at least one circumferential spring coupled to the biocompatible elastic material of the pouch to aid in sealing the connector when the first connector of the first lead assembly is not disposed over the first microstimulator electrode.

4. The method of claim 3, wherein providing at least one circumferential spring coupled to the biocompatible elastic material to aid in sealing the connector comprises providing at least one circumferential spring that is distinguishable from the biocompatible elastic material of the pouch.

5. The method of claim 3, wherein providing at least one circumferential spring coupled to the biocompatible elastic material to aid in sealing the connector comprises providing at least one circumferential spring configured and arranged to collapse a portion of the first connector to seal the first connector when the first connector of the first lead assembly is not disposed over the first microstimulator electrode.

6. The method of claim 3, wherein providing a first connector that comprises a pouch of elastic biocompatible material configured and arranged to seal the first connector comprises providing at least one leaf spring coupled to the biocompatible elastic material of the pouch to aid in sealing the connector when the first connector of the first lead assembly is not disposed over the first microstimulator electrode.

7. The method of claim 6, wherein providing at least one leaf spring coupled to the biocompatible elastic material to aid in sealing the connector comprises providing at least one leaf spring that is distinguishable from the biocompatible elastic material of the pouch.

8. The method of claim 6, wherein providing at least one leaf spring coupled to the biocompatible elastic material to aid in sealing the connector comprises providing at least one leaf spring configured and arranged to collapse a portion of the first connector to seal the first connector when the first connector of the first lead assembly is not disposed over the first micro stimulator electrode.

9. The method of claim 6, wherein providing at least one leaf spring coupled to the biocompatible elastic material to aid in sealing the connector comprises providing at least one leaf spring that is disposed on an exterior surface of the pouch.

10. The method of claim 6, wherein providing at least one leaf spring coupled to the biocompatible elastic material to aid in sealing the connector comprises providing at least one leaf spring that is incorporated longitudinally in walls of the pouch.

11. The method of claim 1, wherein providing a first connector that comprises a pouch of elastic biocompatible material configured and arranged to seal the first connector comprises providing a plug adapted for insertion into the first connector to inhibit fluid ingress into the first connector when the first connector of the first lead assembly is not disposed over the first microstimulator electrode.

12. The method of claim 1, wherein disposing the first connector of the first lead assembly over the first microstimulator electrode comprises electrically coupling a contact of the first lead assembly to the first microstimulator electrode, the contact disposed in the first connector and electrically coupled to the insulated conductor.

13. The method of claim 12, wherein electrically coupling a contact of the first lead assembly to the first microstimulator electrode comprises electrically coupling to the first microstimulator electrode a contact with at least one edge that extends at least partly around the first microstimulator electrode when the first microstimulator electrode is inserted into the connector, wherein the at least one edge facilitates inhibiting fluid ingress into the connector when the first microstimulator electrode is not present in the connector.

14. The method of claim 1, further comprising disposing the first connector of the first lead assembly over the first microstimulator electrode comprises connecting the first lead assembly to the implantable microstimulator via a threaded connection.

15. The method of claim 1, further comprising disposing the first connector of the first lead assembly over the first microstimulator electrode comprises connecting the first lead assembly to the implantable microstimulator via a spring-loaded connection.

16. The method of claim 1, further comprising providing a fixation device configured and arranged for facilitating anchoring of the implantable medical device to patient tissue adjacent to a target stimulation site, wherein the fixation device is provided along the microstimulator.

17. The method of claim 1, wherein providing an implantable microstimulator comprises providing a microstimulator with a second microstimulator electrode disposed along the second end portion of the body.

18. The method of claim 17, further comprising:
providing a second lead assembly, the second lead assembly comprising at least one second remote electrode disposed at a distal end of the second lead assembly, an insulated conductor electrically connected to the at least one second remote electrode, and a second connector disposed at a proximal end of the insulated conductor; and
disposing the second connector of the second lead assembly over the second microstimulator electrode to completely cover the second microstimulator electrode and to electrically couple the insulated conductor of the second lead assembly to the second microstimulator electrode.

19. The method of claim 1, further comprising providing a fixation device configured and arranged for facilitating anchoring of the implantable medical device to patient tissue adjacent to a target stimulation site, wherein the fixation device is provided along the first lead assembly.

* * * * *